(12) United States Patent
Hanna et al.

(10) Patent No.: US 9,439,819 B2
(45) Date of Patent: *Sep. 13, 2016

(54) LOW PROFILE MEDICAL KIT

(71) Applicant: Phokus Research Group, LLC, Rye, NY (US)

(72) Inventors: Robert J. Hanna, San Diego, CA (US); Jonathan M. Gumbert, La Mesa, CA (US); Daniel C. Stein, Cos Cob, CT (US); Noel Edward Sons, San Diego, CA (US)

(73) Assignee: Phokus Research Group, LLC, Rye, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/590,854

(22) Filed: Jan. 6, 2015

(65) Prior Publication Data

US 2015/0216744 A1      Aug. 6, 2015

Related U.S. Application Data

(63) Continuation of application No. 13/447,621, filed on Apr. 16, 2012, now Pat. No. 8,925,115.

(60) Provisional application No. 61/475,803, filed on Apr. 15, 2011.

(51) Int. Cl.
| | | |
|---|---|---|
| *A41D 31/00* | (2006.01) |
| *A41D 1/04* | (2006.01) |
| *A41D 13/00* | (2006.01) |
| *A61F 17/00* | (2006.01) |
| *F41H 1/02* | (2006.01) |
| *A41D 13/01* | (2006.01) |
| *A45F 5/02* | (2006.01) |

(52) U.S. Cl.
CPC ........... *A61F 17/00* (2013.01); *A41D 13/0012* (2013.01); *A41D 13/01* (2013.01); *A41D 31/0055* (2013.01); *A45F 5/022* (2013.01); *F41H 1/02* (2013.01)

(58) Field of Classification Search
CPC ...................... A41D 13/0012; A41D 31/0038; A41D 13/00; F41H 1/02
USPC ....... 2/455, 456, 462, 2.5, 92, 102, 247–253
See application file for complete search history.

(56) References Cited

U.S. PATENT DOCUMENTS

| | | |
|---|---|---|
| 3,634,889 A | 1/1972 | Rolsten |
| 5,014,359 A | 5/1991 | Hanson |

(Continued)

OTHER PUBLICATIONS

Individual Trauma Kit, Practical Tactical, LLC, http://web.archive.org/web/20091029185131/http://www.practicaltactical.net/prostores/servlet/-strse-277/ITK--dsh--Individual-Trauma/Detail, archived by web.archive.org on or before Oct. 29, 2009, 2 pages.

(Continued)

*Primary Examiner* — Bobby Muromoto, Jr.
(74) *Attorney, Agent, or Firm* — Dentons US LLP

(57) ABSTRACT

In a first-aid system including an ultra compact first-aid pouch configured to fit behind the ballistic plates of a protective vest, the first-aid kit is protected from shrapnel and tearing, is easily locatable and removable and does not effect the user's freedom of movement. When the first-aid pouch is removed from its protected location, it presents the first-aid equipment in a logical and easily viewable manner.

31 Claims, 14 Drawing Sheets

(56) References Cited

U.S. PATENT DOCUMENTS

| | | | |
|---|---|---|---|
| 5,219,290 A | 6/1993 | Lapp et al. |
| 5,240,156 A | 8/1993 | Sicotte et al. |
| 5,265,782 A | 11/1993 | McNamara |
| 5,361,412 A | 11/1994 | Perry |
| 5,370,288 A | 12/1994 | Field |
| 5,617,582 A | 4/1997 | Burwell |
| 5,644,792 A | 7/1997 | Tishler et al. |
| 5,657,917 A | 8/1997 | Johnson et al. |
| 5,722,576 A | 3/1998 | Rogers |
| 5,766,715 A | 6/1998 | Garconnet |
| 5,848,700 A | 12/1998 | Horn |
| 5,913,409 A | 6/1999 | Test |
| 5,931,304 A | 8/1999 | Hammond |
| 6,185,738 B1 | 2/2001 | Sidebottom |
| 6,314,579 B1 | 11/2001 | Marcon |
| 6,343,694 B1 | 2/2002 | Parnell et al. |
| 6,350,168 B1 | 2/2002 | Kroll et al. |
| 6,405,378 B1 | 6/2002 | Garner |
| 6,454,097 B1 | 9/2002 | Blanco |
| 6,481,528 B2 | 11/2002 | Antonio |
| 6,874,163 B2 | 4/2005 | Marshall |
| 6,957,738 B2 | 10/2005 | Hammond |
| 7,004,808 B1 | 2/2006 | Nelson et al. |
| 7,896,719 B2 | 3/2011 | Rayles et al. |
| 8,146,787 B2 | 4/2012 | Cragg |
| 8,925,115 B1 * | 1/2015 | Hanna ................ F41H 1/02 2/102 |
| 2001/0052142 A1 | 12/2001 | Marcon |
| 2002/0157165 A1 | 10/2002 | Kroll et al. |
| 2003/0085246 A1 | 5/2003 | Reisman et al. |
| 2003/0101508 A1 | 6/2003 | Marshall |
| 2004/0088780 A1 | 5/2004 | Bachar |
| 2004/0161732 A1 | 8/2004 | Stump et al. |
| 2004/0224582 A1 | 11/2004 | Kroll |
| 2005/0263104 A1 | 12/2005 | Lazarowich |
| 2006/0042990 A1 | 3/2006 | Galuten |
| 2006/0288466 A1 | 12/2006 | Bucheit |
| 2006/0289329 A1 | 12/2006 | Miller |
| 2007/0151624 A1 | 7/2007 | Munz |
| 2007/0232164 A1 | 10/2007 | Swan et al. |
| 2007/0251849 A1 | 11/2007 | Lo et al. |
| 2008/0010730 A1 | 1/2008 | Twito et al. |
| 2008/0043458 A1 | 2/2008 | Desjardin |
| 2008/0078682 A1 | 4/2008 | Clark et al. |
| 2008/0121554 A1 | 5/2008 | Townsend |
| 2008/0121730 A1 | 5/2008 | Calkin |
| 2008/0171311 A1 | 7/2008 | Centen et al. |
| 2008/0249482 A1 | 10/2008 | Erez |
| 2008/0277443 A1 | 11/2008 | Thiriot et al. |
| 2008/0280516 A1 | 11/2008 | Rayles et al. |
| 2009/0031467 A1 | 2/2009 | Swindells et al. |
| 2009/0089087 A1 | 4/2009 | Kotecki |
| 2009/0152159 A1 | 6/2009 | Beeman |
| 2009/0205996 A1 | 8/2009 | Celis |
| 2009/0307878 A1 | 12/2009 | Kadas |
| 2010/0043112 A1 | 2/2010 | Khandelwal |
| 2010/0252598 A1 | 10/2010 | Cragg |
| 2011/0083248 A1 | 4/2011 | Johson |
| 2011/0204114 A1 | 8/2011 | Miller |
| 2012/0018478 A1 | 1/2012 | Hanna et al. |

OTHER PUBLICATIONS

Individual Combat Medical Kit, Practical Tactical, LLC, http://web.archive.org/web/20091029185136/http://www.practicaltactical.net/prostores/servlet/-strse-278/ICMK--dsh--Individual-Combat/Detail, archived by web.archive.org on or before Oct. 29, 2009, 2 pages.

Combat Casualty Response Kit-Medic/Leg Rig, North American Rescue, http://www.narescue.com/Medic_Leg_Rig_Kit_(CCRK)-CN31912CC814EB.html, accessed Oct. 17, 2012, 2 pages.

Individual Patrol Officer Kit (IPOK), North American Rescue, http://www.narescue.com/Individual-Patrol-Officer-Kit-IPOK-P347C122.aspx, accessed Oct. 17, 2012, 2 pages.

* cited by examiner

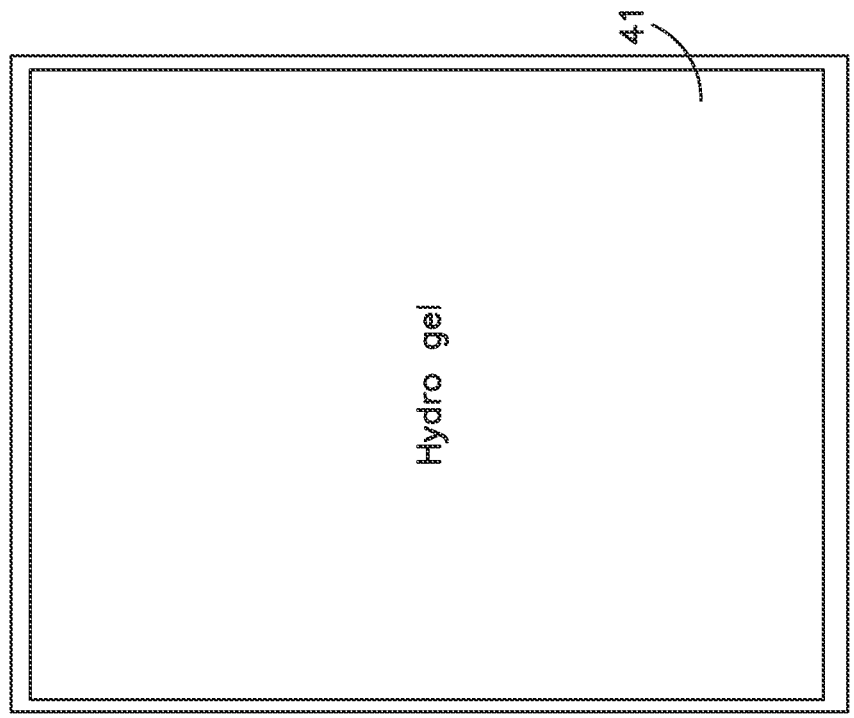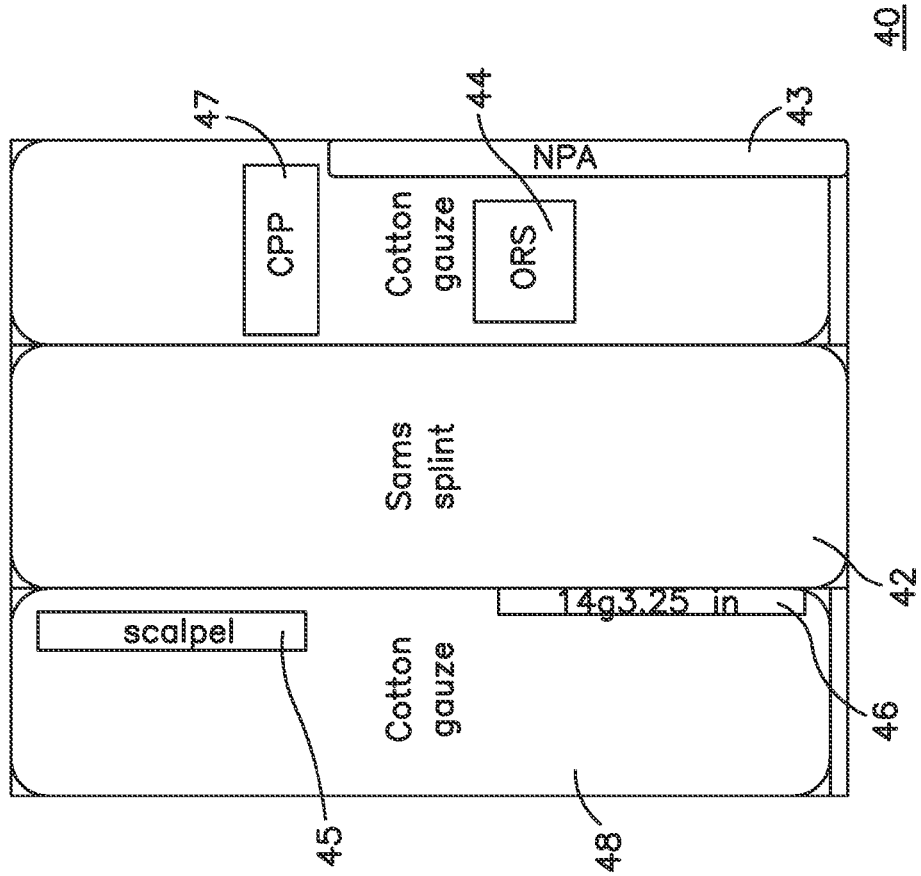

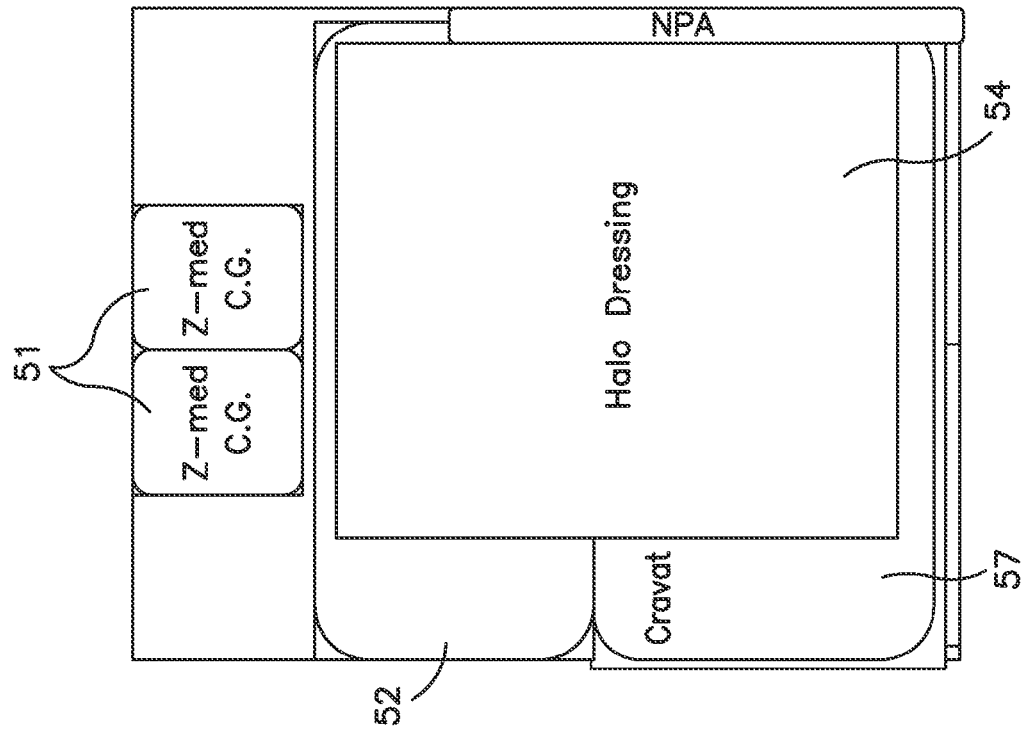
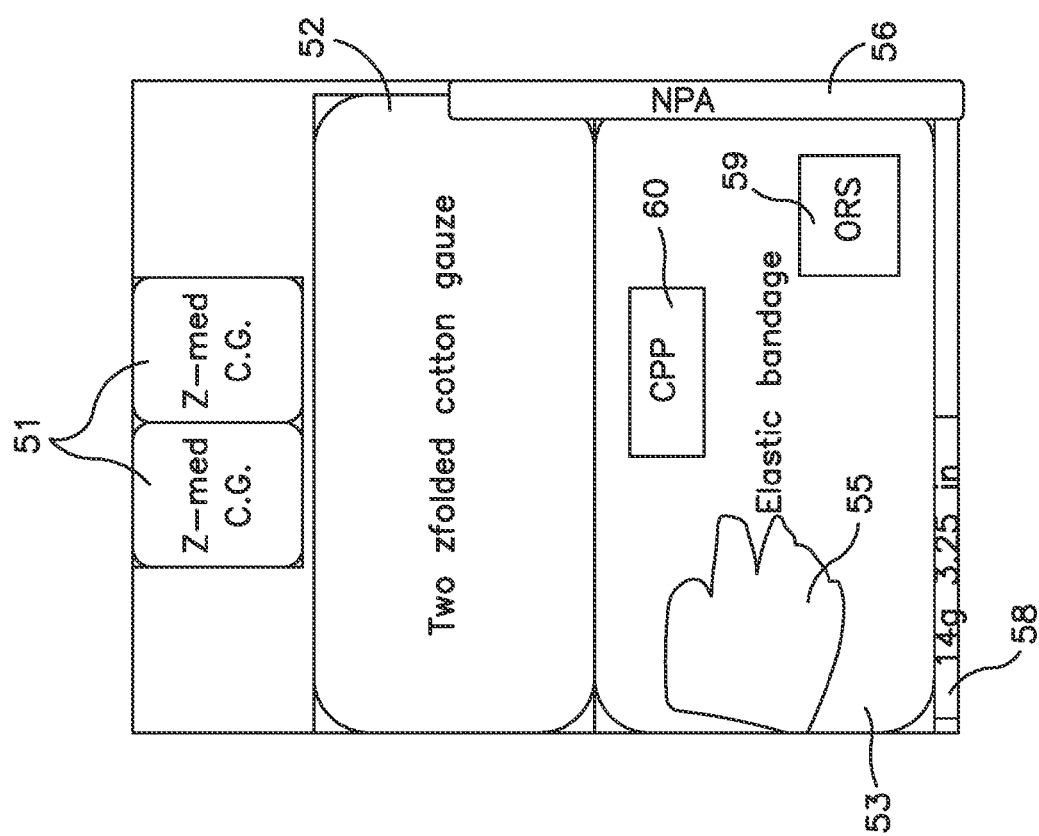

LOW PROFILE MEDICAL KIT

CROSS REFERENCE TO RELATED MATTERS

The present application is a Continuation of U.S. Nonprovisional application Ser. No. 13/447,621 filed 16 Apr. 2012, now U.S. Pat. No. 8,925,115 issued 6 Jan. 2015, which claims the benefit of U.S. Provisional Application Ser. No. 61/475,803 filed 15 Apr. 2011; each of which is incorporated herein by reference in its entirety for all purposes.

TECHNICAL FIELD

The present invention relates to first-aid systems, and more particularly, to utilizing a low profile ultra slim emergency first-aid kit that can be easily stored and carried by a person.

BACKGROUND

First-aid kits generally contain items intended to be used as a means to quickly and effectively respond to accidents or injuries when away from traditional medical emergency facilities. Such kits are intended to be used either by the injured party or to aid someone else who has been injured. To be effective therefore, a first-aid kit must be lightweight, portable, accessible, and must contain the necessary equipment to treat accidents or injuries that may occur based on the situation and environment. Nowhere is this more critical then in a military or law enforcement environment, where the threat of accident or injury is often severe and access to on site medical treatment limited.

Traditionally, military personal have been provided with individual first-aid kits (IFAK) during times of military deployment. Such kits are typically housed in cloth bags or pouches and are designed to be worn on the outside of a uniform. Such IFAKs are intended to increase an individual soldiers capability to provide self-aid or buddy-aid on the battlefield. The kits typically contain first-aid equipment intended to treat sever hemorrhage and inadequate airway injuries, the two leading cause of battlefield fatalities.

Current first-aid kits are either deployed on a belt strap, back pouch, or leg strap to allow for freedom of movement and access to the contents of the pouch. This often makes it difficult for a soldier or law enforcement officer to get to the contents of the pouch, for example, when in a sitting position or inside a vehicle. Additionally, if a wounded soldier or officer needs to be dragged out of harms way, having the kit mounted on the exterior of a uniform often results in the kit being torn off and lost in the process. Furthermore, in the event of an explosion, kits located on the outside of a uniform are often blown off or destroyed due to shrapnel and are therefore of no value to the injured person or to those treating them.

Another shortfall of the current first-aid kits, is that during times of high stress and rapid combat deployment, it may be inadvertently left behind, as it is one more piece of equipment that a solider or enforcement officer must remember to attach to a uniform. Similarly, because of the lack of uniformity in placement on a user's person, it is often hard to locate or determine if a victim is in possession of a first-aid kit, as soldiers or law enforcement officer often are deployed with many types of gear in many similar types of pouches and bags. In situations where seconds may determine the chance to save a life, such confusion cannot be tolerated. Further, due to the external and bulky mounting of existing kits, they tend to get in the way of operations and inhibit the wearers ability to quickly and efficiently get into and out of confined spaces and quarters.

Finally, existing IFAKs are often disorganized and the contents are simply thrown into a bag. The contents are randomly mixed inside, requiring the entire contents to be emptied during an emergency situation so that a person administering aid can locate the item or items required under the circumstances. This does not allow the user to administer first-aid in a logical order, may lead to confusion and lost time.

Accordingly, a need exists for a first-aid kit, that will not be left behind, will not be torn or ripped off during maneuvers or damaged due to shrapnel, is light weight, uniformly deployable, presents the contents in a logical fashion and is easily accessible by both the carrier or another party. The apparatus and systems illustrated address those needs.

SUMMARY

Typical protective vests are manufactured from "softarmor" materials such as Kevlar® or other "bullet proof" materials and offer a level of protection to the wearer sufficient to offer protection in many situations. For the additional security required in today's military and law enforcement applications, however, soft armor is often insufficient against military munitions and shrapnel. Accordingly, many protective vests or body armor vests contain a series of external pockets on the front, back and sides of the vest for adding additional body armor such as metal or ceramic plates, also known as ballistic plates or hard armor. The plates are usually placed to cover particularly vulnerable parts of the body such as the heart, chest, and back regions, thereby providing protection to the vital organs. The pockets may also be provided on internal portions of the vests to allow the ballistic plates to be located between the vest and the user.

The vast majority of soldiers in combat and law enforcement personnel now wear some sort of protective vest to prevent bodily injury from bullets and shrapnel. The configuration and protection afforded by such vests can be exploited to remedy the shortfalls of existing individual first-aid kits. By configuring a first-aid pouch to fit behind the ballistic plates in front of or behind the wearer, either in the existing pockets of the vest or between the hard and soft armor or on the inside of the vest itself, adjacent the user, the first-aid kit can be protected from shrapnel and tearing, is easily locatable and removable and does not effect the user's freedom of movement, and when removed from the vest, presents the first-aid equipment in a logical, easily viewable manner. In order to implement such a system however, IFAKs must be ultra thin and not add any significant bulk to the wearers protective vest. Must be easily accessible and removable and should present the contents in an organized manner.

One embodiment discloses a first-aid system comprising a protective vest containing a first ballistic plate to be worn by a user, and a first pouch for holding first-aid equipment, wherein the protective vest contains an internal surface and an external surface, the external surface containing a pocket for locating the first ballistic plate, and wherein the first pouch is located between the ballistic plate and the user, either in the internal pocket on the exterior of the vest or on the interior of the vest, for example, in an internal pocket or attached to the inside of the vest. The first aid pouch may be located in a pocket or attached or connected to the vest or ballistic plate using any type of attachment method, including glue, hook and loop fasteners, snaps, tape, zippers, magnets, springs, clips, fastecs, safety pins, or any other type of connector or attachment mechanism now know or later developed. The first aid system may alternatively or additionally include a second pouch located at the rear of the vest. The second pouch may be attached to the vest or ballistic plate in the same manner as the first pouch or in a different manner.

In another embodiment the individual first-aid kit or kits are vacuum sealed into low profile pouches, configured to be deployed in locations between the ballistic plates of a user's protective vest and the user thereby providing the wearer with an easily locatable, individual protected first-aid kit.

In a further embodiment, the kits are releasably attached to the inside of the vest and contain a handle to allow the user or the wearer to quickly and easily locate and remove the kits when needed. Alternatively, the pouches or kits may include a rip cord that when pulled releases the pouch from the connectors or the pocket.

In an embodiment, the first-aid kits are releasably attached to the ballistic plates inserted into the pockets of the vest allowing the user or the wearer to quickly and easily locate and remove the kits when needed.

In another embodiment, the low profile first-aid kit for emergency medical treatment comprises a sealable pouch, a substantially planar base portion, and a plurality of first-aid items arranged in a prioritized order detachably secured to the substantially planar base portion. Alternatively, the base portion may be malleable so as to conform to the shape of the user at the location of deployment.

In yet another embodiment, the first-aid equipment is detachably mounted to a substantially planar board and arranged in a prioritized order to allow the user to administer first-aid in a logical order. Alternatively, the part that the first-aid equipment is mounted to may be malleable so as to conform to the shale of the user at the location of deployment.

BRIEF DESCRIPTION OF THE DRAWINGS

The system and apparatus, in accordance with one or more embodiments, is described in detail with reference to the following drawings. The drawings are provided for purposes of illustration only and merely depict typical or example embodiments. These drawings are provided to facilitate the reader's understanding and shall not be considered limiting of the breadth, scope, or applicability of the disclosure. It should be noted that for clarity and ease of illustration these drawings are not necessarily made to scale.

Some of the figures included herein illustrate various embodiments from different viewing angles. Although the accompanying descriptive text may refer to such views as "top," "bottom" or "side" views, such references are merely descriptive and do not imply or require that the embodiment be implemented or used in a particular spatial orientation unless explicitly stated otherwise.

FIGS. 9A and 9B are front and rear views, respectively, of a first-aid pouch in accordance with an embodiment of the present invention;

FIGS. 10A and 10B are front and rear views, respectively, of a first-aid pouch in accordance with an embodiment of the present invention;

The figures are not intended to be exhaustive or limited to the precise form disclosed. It should be understood that the invention can be practiced with modification and alteration, and that it is limited only by the claims and the equivalents thereof.

DETAILED DESCRIPTION

The present invention is described herein in terms of example embodiments. Descriptions in terms of these embodiments are provided to allow the various features of the invention to be portrayed in the context of an exemplary application. As will be clear to one of ordinary skill in the art, the invention can be implemented in different and alternative embodiments without departing from the spirit of the invention.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Figure 1:
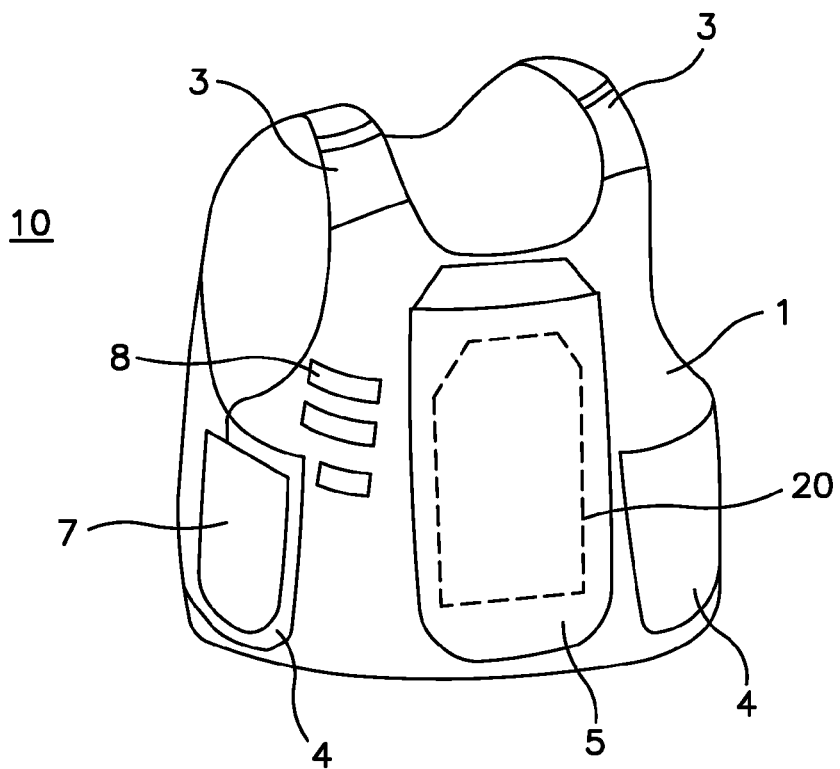
FIG. 1 is a view of the exterior front section of a typical protective vest.
Figure 2:
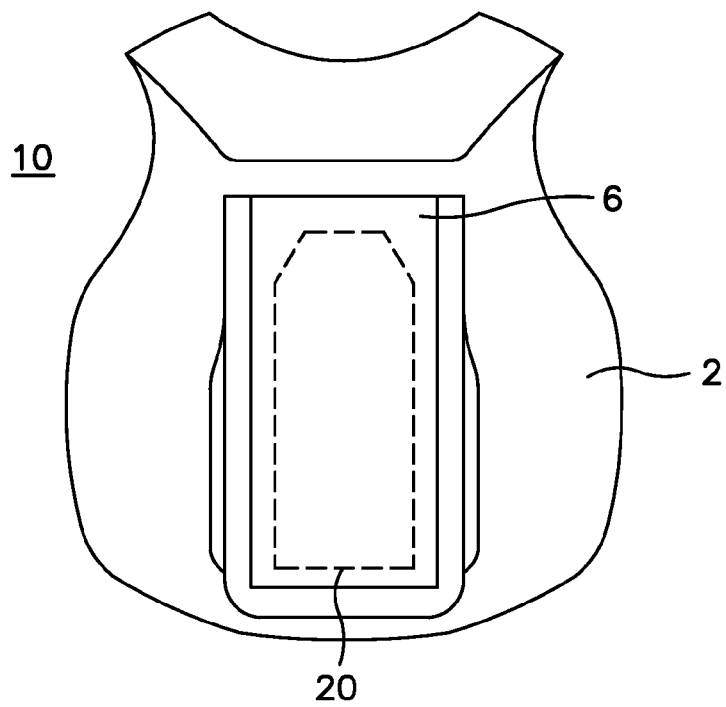
FIG. 2 is a view of the exterior rear section of a typical protective vest.

FIG. 1 depicts the outside front of protective vest 10. FIG. 2 depicts the outside back portion of protective vest 10. Vest 10 includes chest portion 1, back portion 2, shoulder straps 3, side closures 4, front ballistic plate pocket 5, rear ballistic plate pocket 6, side pockets 7, and equipment straps 8. Typical vests are modular in nature and may also include additional ballistic plate pockets, ballistic collars, lower back plates, and/or groin protection portions as well. The inclusion or exclusion of such additional components is not necessary for practicing the embodiments disclosed, however, utilizing the additional areas of protection afforded by these additional features, would be within the spirit of the invention.

A user wishing to wear protective vest 10 will typically slip the vest over the head so that chest portion 1 is located on the front of the body and back portion 2 is located over the back of the body. Utilizing side closures 4, the vest 10 can be adjusted to fit the user snugly. Typically, side closures 4 are held in place with hook and loop type fasteners or the like. Protective vest 10 maybe a cloth vest or may be integrally manufactured with a layer of soft armor such as Kevlar®.

Figure 5:
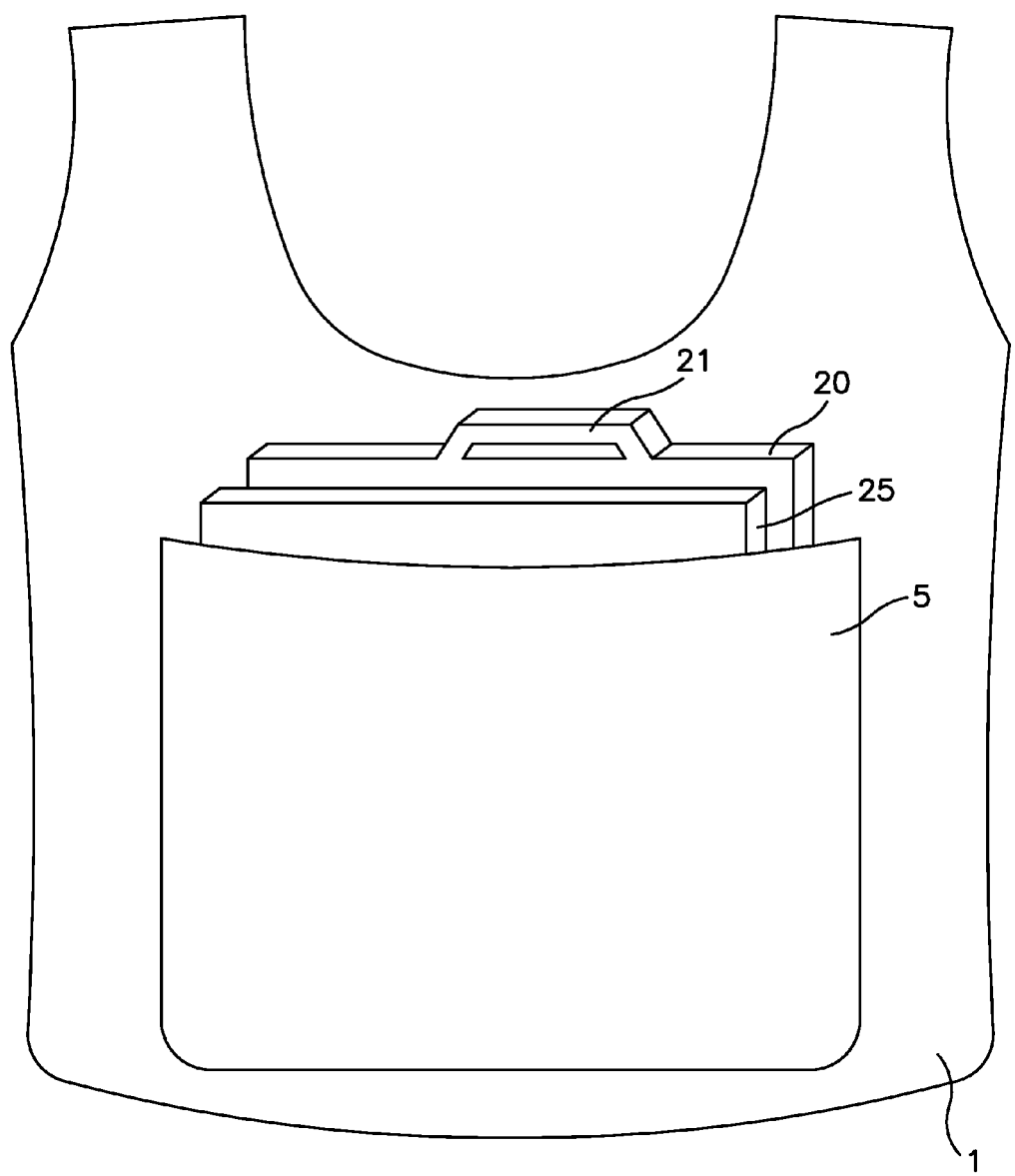
FIG. 5 is a close up view of a pocket on the exterior of the protective vest.
Figure 6:
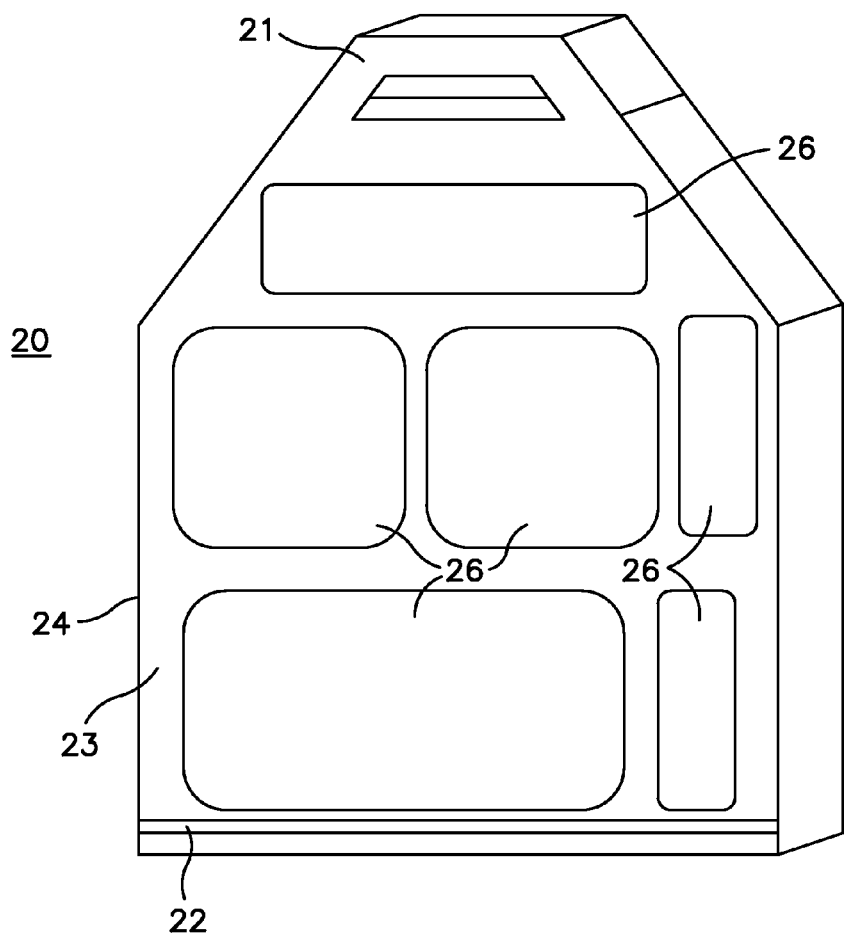
FIG. 6 is a perspective view of a typical first-aid pouch in accordance with an embodiment of the present invention.

In this embodiment, first-aid pouch 20, as depicted in FIGS. 5 and 6 may fit inside front ballistic pocket 5 behind ballistic plate 25 and in front of the soft armor or Kevlar® layer of protective vest 10. As seen in FIG. 5, first-aid pouch 20 is protected behind ballistic plate 25 yet is easily removable by the wearer or anyone needing to utilize the first-aid pouch.

Likewise, in FIG. 2, first-aid pouch 20 is located in rear ballistic plate pocket 6 between the ballistic plate (not shown) and the soft armor layer of protective vest 10 closest to the wearers body. In this location, the first-aid pack is protected from shrapnel and bullets, yet easily accessible as a buddy-pack first-aid kit when required. As will be appreciated by those skilled in the art, as long as the first-aid pack is located between a ballistic plate and the user or between the hard and soft armor, the location of the pockets in the protective vest can be modified and altered without departing from the spirit of the invention.

Figure 3:
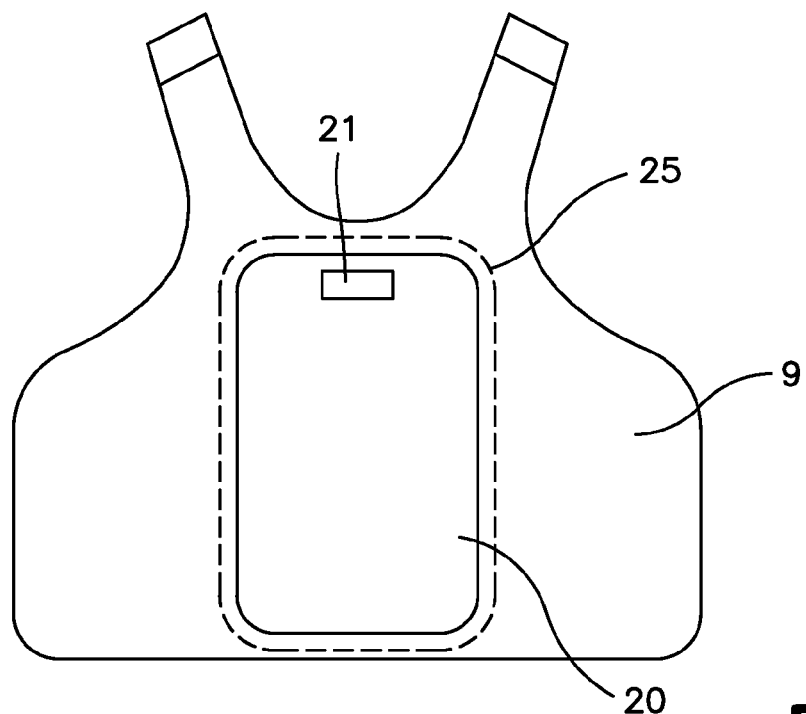
FIG. 3 is a view of the inside of a front section of a typical protective vest.
Figure 4:
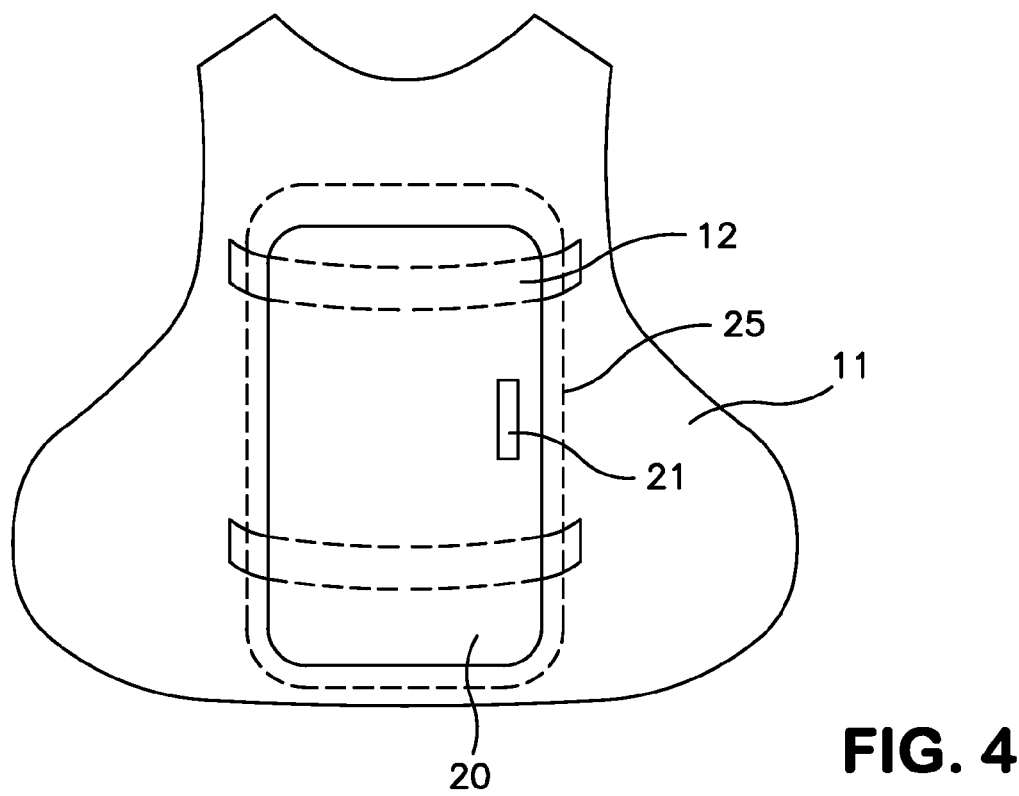
FIG. 4 is a view of the inside of a rear section of a typical protective vest.

In another embodiment, the first-aid pouch is located on the inside of the vest adjacent the wearers body behind the hard and soft armor. In this configuration, the first-aid pouch is not within a ballistic plate pocket, but still behind ballistic plate 25 which is inserted in the outside pocket of protective vest 10. As seen in FIG. 3, first-aid pouch 20 can be located on inside front 9 of protective vest 10. Likewise, as seen in FIG. 4 first-aid pouch 20 can be located in the inside rear 11 of protective vest 10. In either configuration, the first aid pouch 20 is located behind the hard and soft armor. First-aid pouch 20 can be attached to the inside of the vest utilizing connectors 12. Connector 12 can be any type of attachment mechanism that allows first-aid pouch 20 to be releasably connected to inside front 9 or inside rear 12. Typically, a hook and loop type connector can be used, but other connectors such as magnets, springs, clips, fastecs, or any other suitable connector capable of fastening the pack to the vest may be utilized.

As noted in FIGS. 3 and 4, first-aid pouch 20 is directly behind the ballistic plate 25 (represented by the dashed line) located on the exterior surface of the ballistic vest in a pocket. In this manner, the first-aid pouch is protected from any bullets or shrapnel while still remaining easily accessible to the wearer. To improve location and ease removal, handle 21 maybe molded or formed in the first-aid pouch by any known methods available.

As seen in FIG. 5, first-aid pouch 20 is completely protected by ballistic plate 25, even when it is located on the exterior of the protective vest 10, by placing it in front ballistic plate pocket 5 of chest portion 1. In this configuration, handle 21 also allows the user easy access to the first-aid pouch when required.

FIG. 6, shows first-aid pouch 20 containing handle 21, opener 22, base, 23, pouch 24 and first-aid items 26. Handle 21 may be located on the top, bottom or sides of first-aid pouch 20 and may be integrated in the pouch itself or be attached to the outside of the pouch provided it allows easy and efficient removal of pouch 20 from its stored location. Likewise, opener 22 may be a tear away strip, rip cord, zip seal, tape or any other means that allows easy and quick access to the contents of pouch 20. Opener 22 may be a single use device or may allow pouch 22 to be resealed after use. Opener 22 may be located anywhere on pouch 20 and is not limited to the location shown.

First-aid items 26 are arranged on base 23 in a prioritized order that allows the user to provide first-aid in an orderly manner without having to search through all the first items to locate the required first-aid item 26. The base 23 made comprise the same material as the remainder of the first aid pouch or may comprise a different material. First-aid pouch 20 is typically composed from plastic that forms a bag 24 over first-aid items 26 and base 23. Once all the desired contents are placed within bag 24, the pouch is vacuum sealed to reduce the overall thickness and bulk of the first-aid pouch 20.

Figure 7:
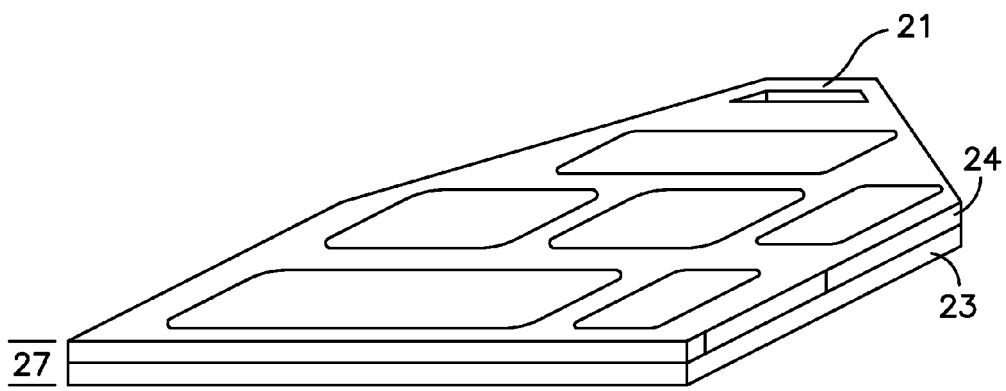
FIG. 7 is a further perspective of the first-aid pouch of FIG. 6 in accordance with an embodiment of the present invention.

As depicted in FIG. 7, ideally, thickness 27 of first-aid pouch 20 is between about 0.2 and 1.0 inches, with the front first-aid kit pouch ideally being between about 0.2 and 0.4 inches or less and the back first-aid pouch being between about 0.2 and 0.04 inches or less. Bag 24 is typically constructed of clear plastic film, to allow the user to view the contents, however, any plastic film, such as a reflective film (Mylar®) or a tinted film, would be acceptable, as long as it is capable of being vacuum sealed. Reflective film such as Mylar® could potentially offer an additional thermal barrier to the wearer, and act as an ad hoc heat shield to aid with hypothermia, as such films typically reflect heat and light in the infrared spectrum.

Front, "self-aid," and rear, "buddy-aid," kits can contain similar or different first-aid supplies, based on the expected mission and conditions. Typically, a front first-aid kit could contain combat gauze S-fold dressings, Kerlix cotton gauze S-fold dressings, a HALO dressing, a 14 G IV catheter, gloves, NPA Adjustable airway, pills, dosage information, Tactical Casualty Combat Care (TCCC) card and safety pins. Similarly, a buddy-aid kit could include a piece of hydro-gel, SAMs splints, Kerlix cotton gauze S-fold dressings, 14 G IV catheter, and monofilament line. Additional items such as scalpels, cravats, and elastic bandages may also be included depending on the environment and expected mission.

Figure 8B:
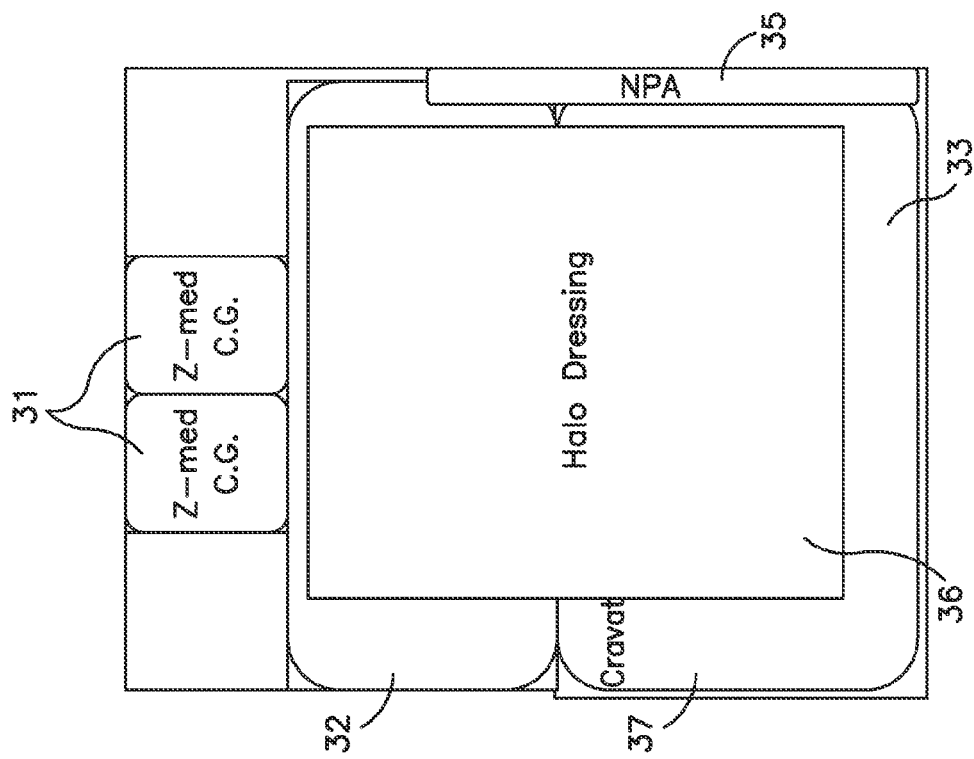
FIGS. 8A and 8B are front and rear views, respectively, of a first-aid pouch in accordance with an embodiment of the present invention.
Figure 8A:
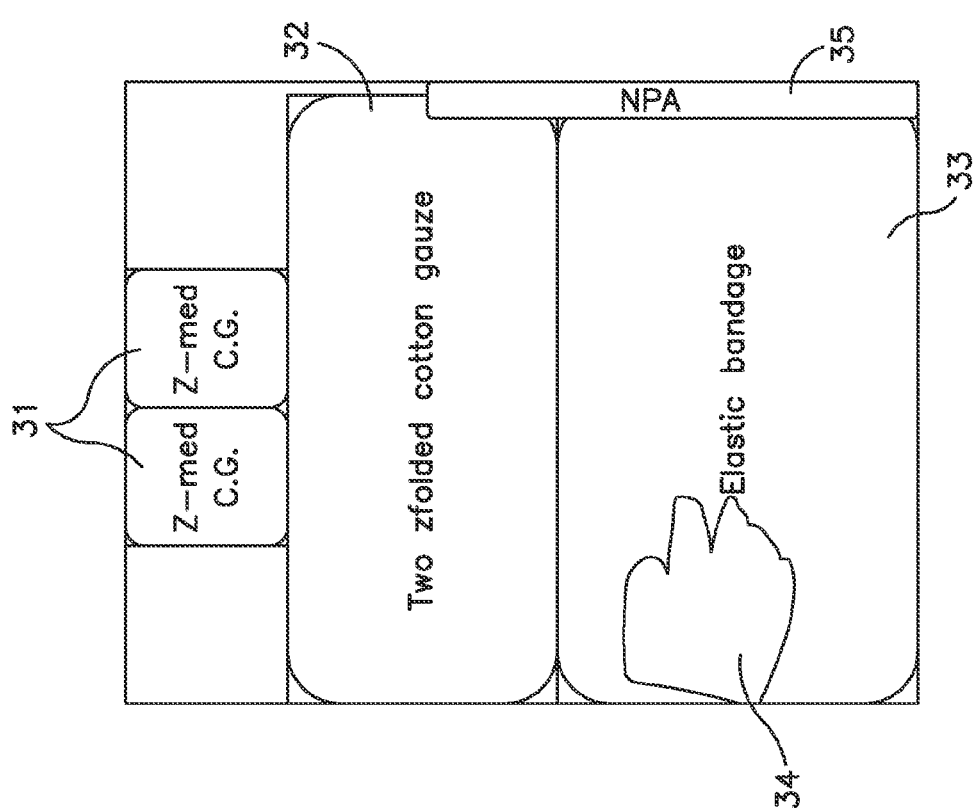

FIGS. 8-11, depict some kits based on the expected missions. These figures and the accompanying descriptions, however, in no way limit the scope of the claims and are merely included as exemplars of possible first-aid kit combinations. FIGS. 8 and 9 depict a typical two day or stay over day kit combination which will suit the needs of the majority of military operations. Such a two-day kit combination would be utilized where evacuation of wounded persons could be delayed. FIGS. 8a and 8b depict both sides of front kit 30. Front kit 30 contains two Z-Med combat gauzes 31, two Kerlix cotton gauzes 32, four inch elastic bandage 33, gloves 34, nasopharyngeal airway (NPA) 35, Halo dressing 36 and cravat 37. FIGS. 9a and 9b depict front and back views of back kit 40. Back kit 40 contains 8"×10" sheet of hydrogel 41, eighteen inch SAM splint 42, NPA 43, oral re-hydrating salt pack 44, #10 scalpel 45, 14 G IV catheter wound with wire 46, combat pill pack 47 (containing for example, medicine, casualty card and safety pins), and two Kerlix cotton gauzes 48.

Another typical kit configuration, includes the single pouch helicopter assault force (HAF) kit depicted in FIG. 10. This single pouch is intended for mission profiles with ground evacuation times between one and two hours. FIG. 10 depicts typical HAF kit 50. FIGS. 10a and 10b depict front and back views of HAF kit 50. HAF kit 50 is typically a front plate kit but as explained previously, it may be deployed anywhere on the body of a wearer without departing from the spirit of the invention, as long as it is placed behind a ballistic plate and adjacent to the users body. HAF kit contains, two Z-Med combat gauzes 51, two Kerlix cotton gauze 52, four inch elastic bandage 53, Halo dressing 54, gloves 55, NPA 56, cravat 57, fourteen gauge IV catheter wound with wire 58, oral re-hydrating salt pack 59 and combat pill pack (CPP) 60.

Figure 11B:
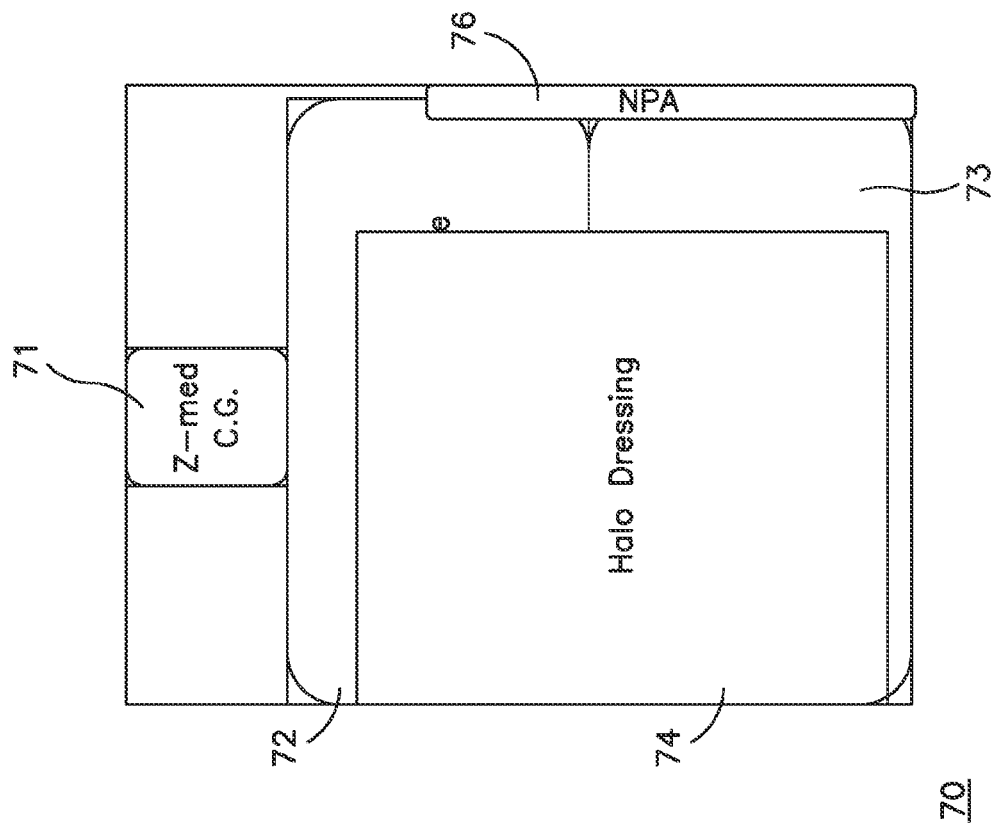
FIGS. 11A and 11B are front and rear views, respectively, of a first-aid pouch in accordance with an embodiment of the present invention.
Figure 11A:
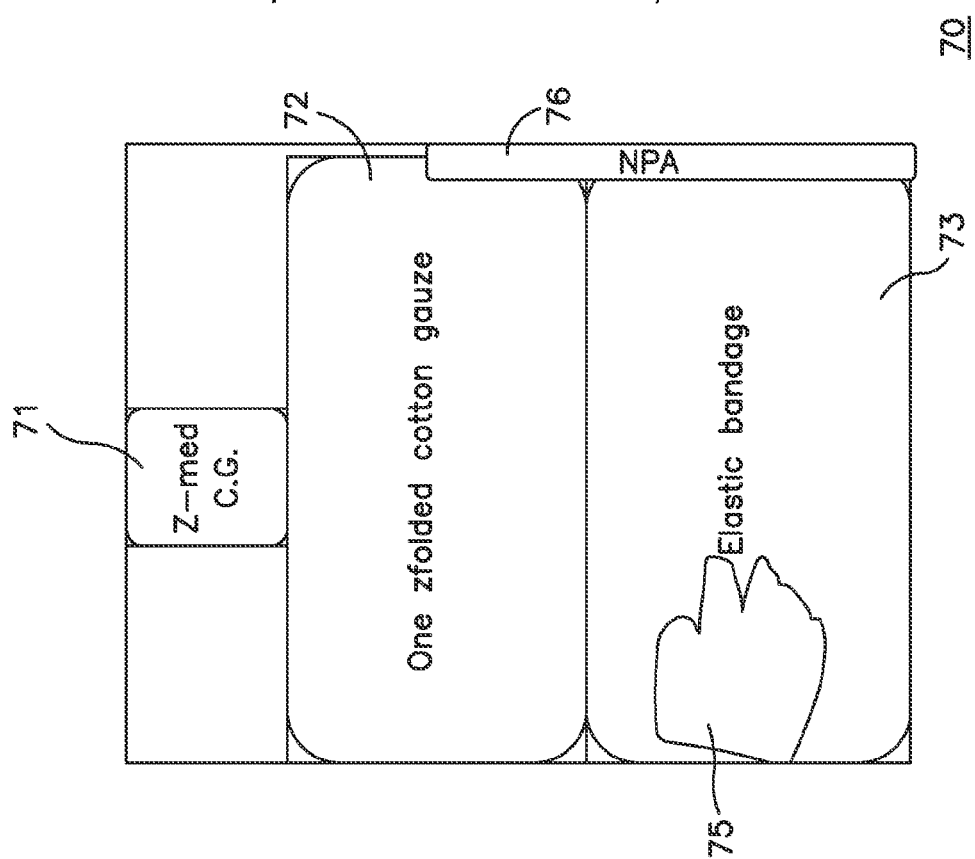

FIG. 11 depicts another typical single pouch kit intended for short missions of less then 1 hour which might be utilized by law enforcement or a military unit with dedicated air support or other quick evacuation means. FIG. 11 depicts typical short mission kit 70. FIGS. 11a and 11b depict front and back views of short mission kit 70. Kit 70 is typically a front plate kit and contains, Z-Med combat gauze 71, Kerlix cotton gauze 72, four inch elastic bandage 73, Halo dressing 74, gloves 75, NPA 76, and combat pill pack (not shown).

Figure 12:
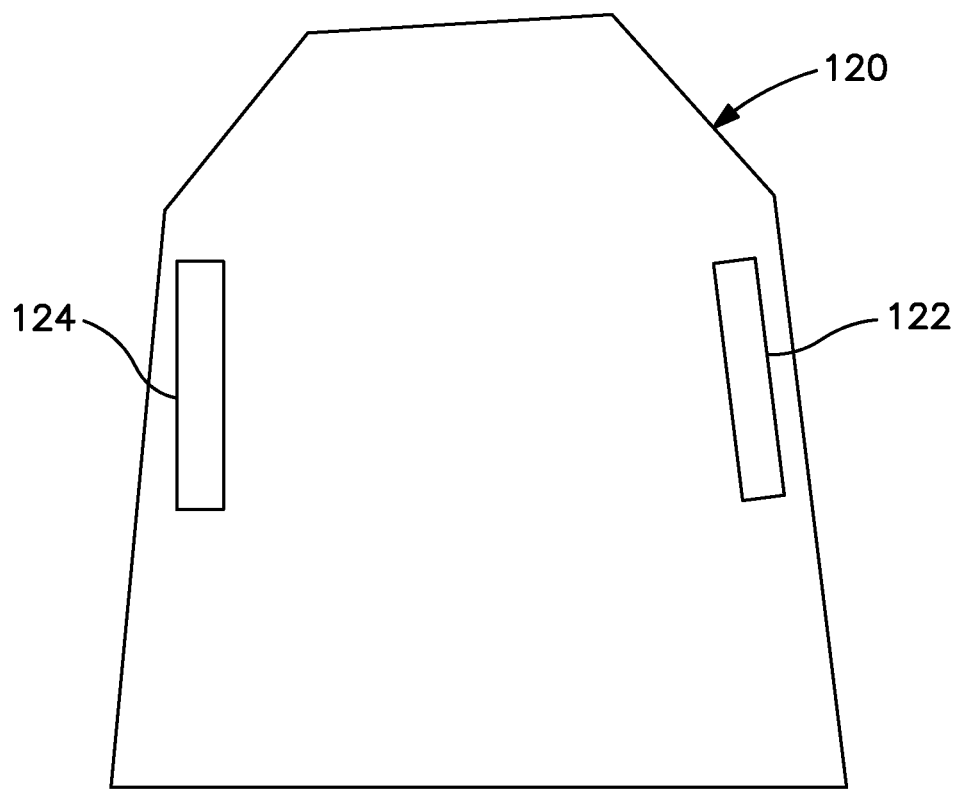
FIG. 12 is a top view of a typical ballistic plate showing first-aid Pouch attachment points in accordance with one embodiment.

FIG. 12 shows ballistic plate 120 and first-aid pouch mounting points 122 and 124. Mounting points 122 and 124 may be any type of fasteners capable of releasably holding a first-aid pouch (not shown) attached to the ballistic plate 120. For example, mounting points 122 and 124 may include glue, hook and loop fasteners, snaps, tape, zippers, magnets, springs, clips, fastecs, safety pins, or any other type of connector or attachment mechanism now know or later developed that is capable of holding the first-aid pouch to the ballistic plate 120. It should be understood, that the locations of fasteners as well as the number of fasteners required is not limited to those shown in FIG. 12. Fasteners 122 and 124 could be located at the top and bottom of ballistic plate 120, or a single fastener could be placed in the middle of plate 120. Similarly, three of four fasteners could be placed around the perimeter of ballistic plate 120 to hold the first-aid pouch.

Figure 13:
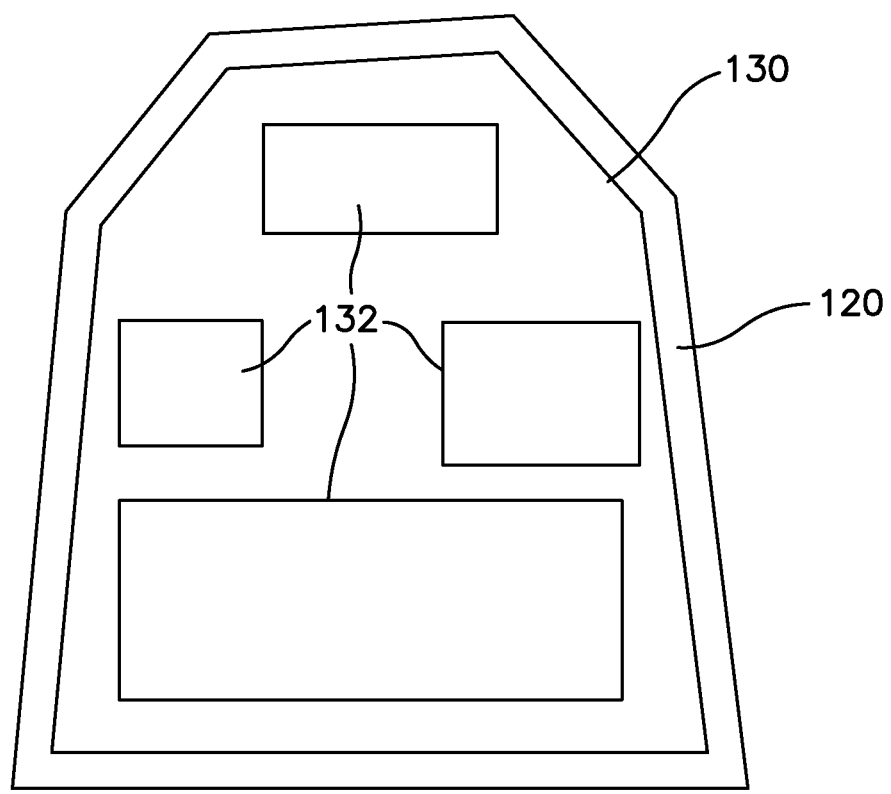
FIG. 13 is a top view of a first-aid pouch mounted to a ballistic plate in accordance with an embodiment of the invention.

FIG. 13 depicts first-aid pouch 130 containing first aid supplies 132 affixed utilizing fasteners 122 and 124 to ballistic plate 120.

Figure 14:
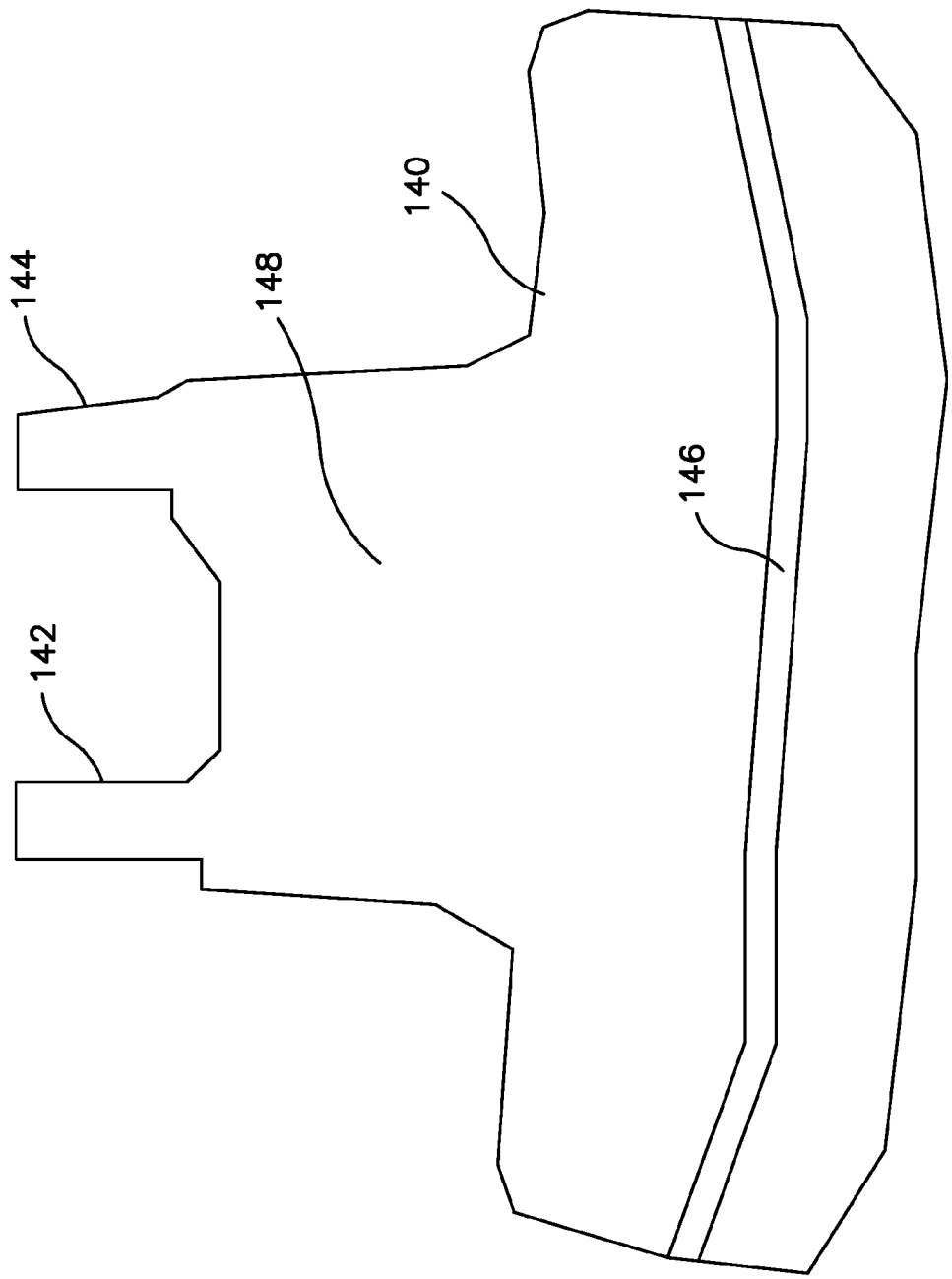
FIG. 14 is a view of the exterior front section of a protective vest.

FIG. 14 depicts the user side view of an alternative type protective vest 140. Protective vest 140 may be worn by the user by placing straps 142 and 144 over the head so that chest section 148 is centered on the front of the wearers body. Protective vest 140 is typically made from cloth or some other pliable material but typically is not constructed from any form of soft or hard armor. Protective vest 140 contains flap 146, which may be held together utilizing hook and loop materials such as Velcro® or may be held together utilizing snaps, zippers, or any other clips or fasteners that will keep flap 146 closed.

Figure 15:
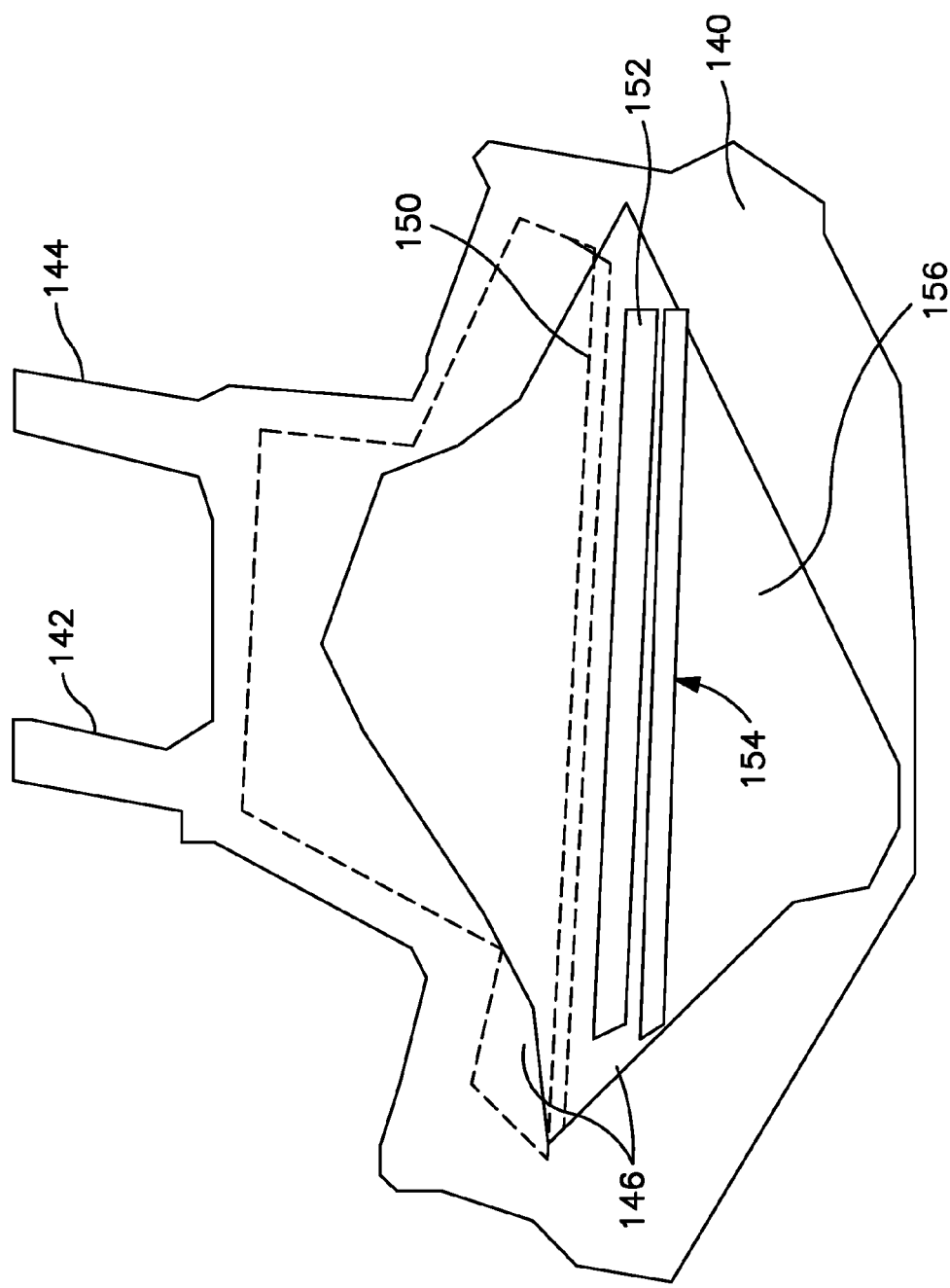
FIG. 15 is a view of the vest of FIG. 14 with its internal pocket open and a ballistic plate and first-aid pouch installed.

FIG. 15 depicts the user side of protective vest 140 with flap 146 in an open position. In operation, a user will slip ballistic plate 154, first-aid pouch 152 and soft armor layer 150 inside the cavity 156 created by opening flap 146. As can be seen in FIG. 15, first-aid pouch 152 is located between ballistic plate 154 and soft armor layer 150, In this manner, the first aid pouch 152 is protected from bullets or shrapnel by ballistic plate 154 and the user is protected from any sharp objects or instruments located in first-aid pouch 152 by soft armor layer 150.

Figure 16:
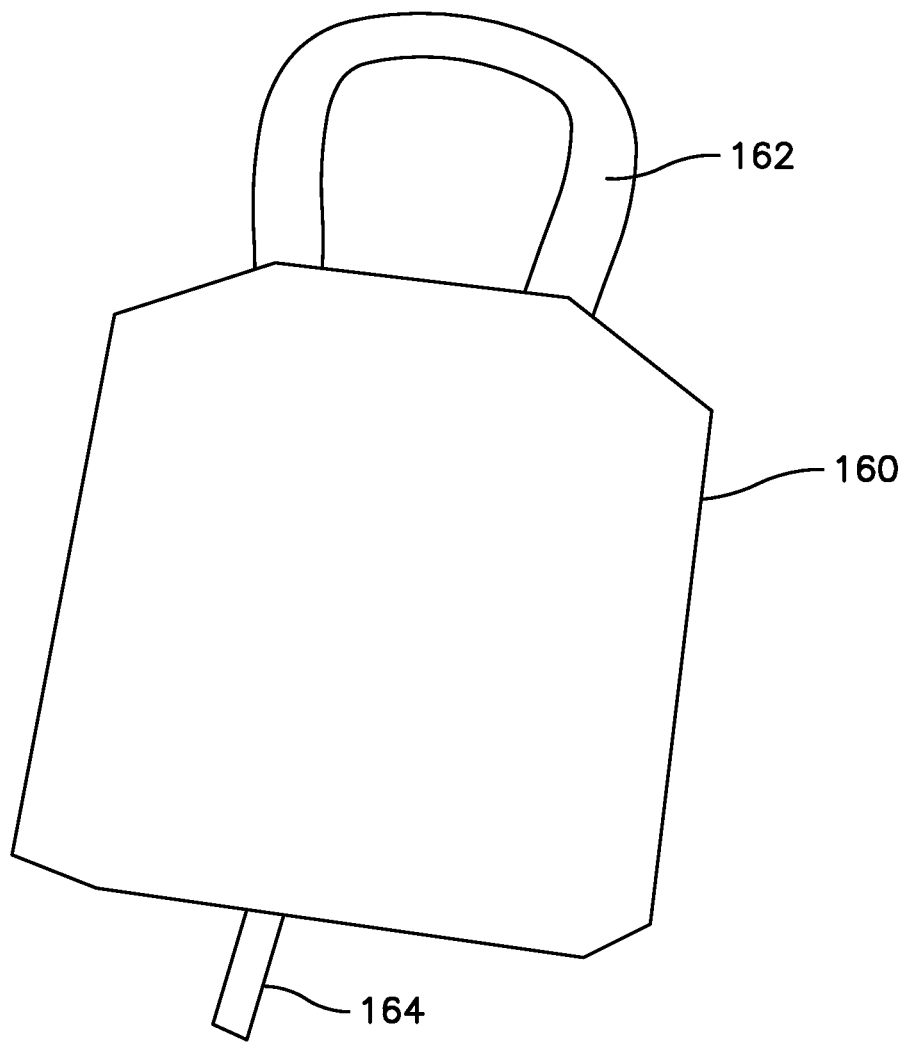
FIG. 16 is a view of a plate holder to be worn over the user's head.
Figure 17:
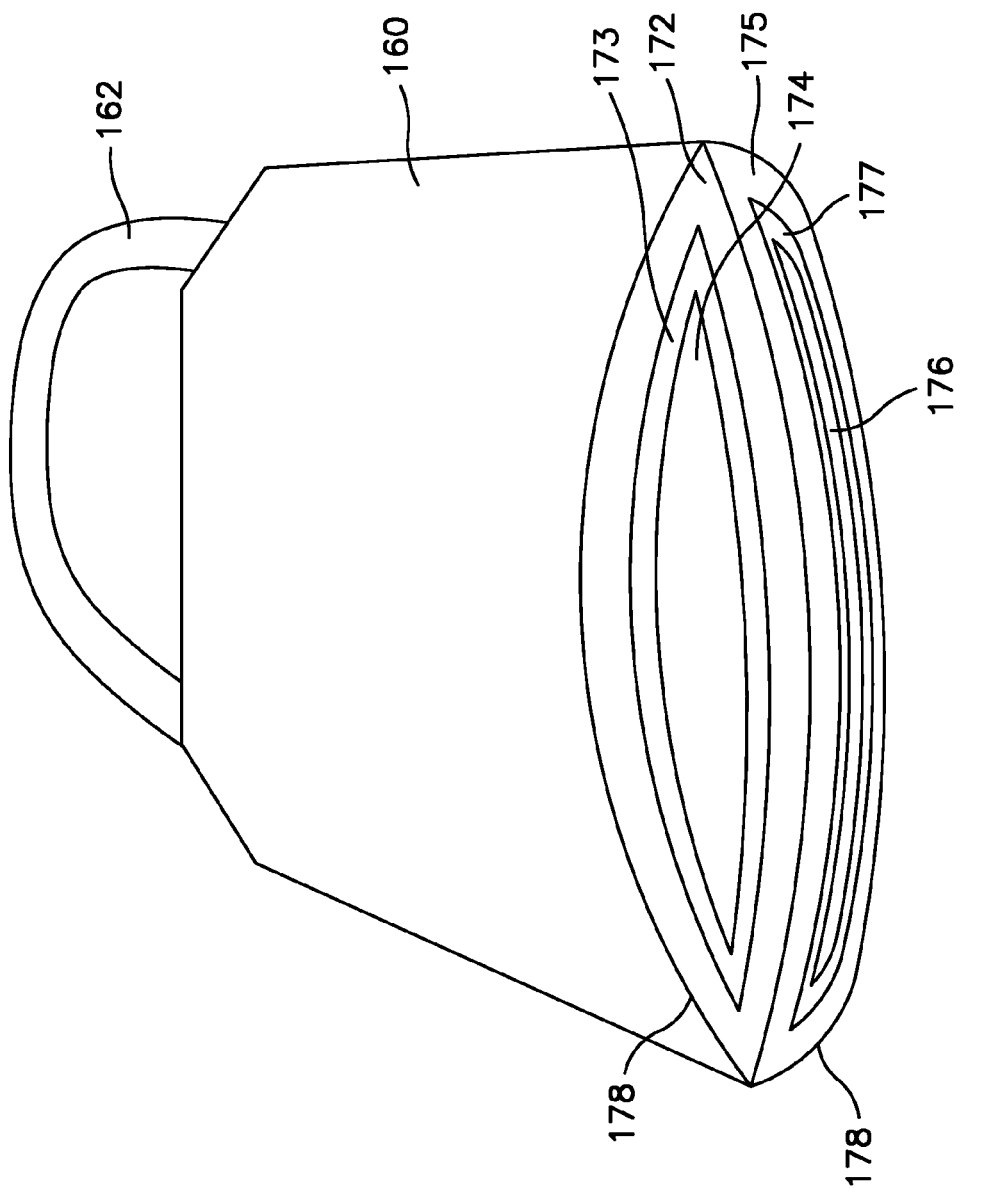
FIG. 17 is an open end view of the user side of the plate holder of FIG. 16 with a ballistic plate and first-aid pouch installed.

FIG. 16 depicts a ballistic plate carrier 160. Plate carrier 160 is intended to be worn around the user's neck by strap 162 to offer additional protection to the vital region of the wearer. Pull tab 164 located at the bottom of plate carrier 160 opens pouch 178. FIG. 17 depicts an end view of the user side of plate carrier 160 with pouch 178 in the open position. Internal to plate carrier 160 is soft armor pouch 172 which creates pocket 173 and ballistic pouch 175 which creates pocket 177. In this configuration, first-aid pouch 174 fits into soft armor pouch 172 and ballistic plate 176 fits into pocket 177. In this manner, first-aid pouch 174 is located behind ballistic plate 176 thereby protecting it from potential damage due to shrapnel or bullets.

In operation, a user of plate carrier 160 desiring to gain access to first-aid pouch 174 would pull on tab 164 to open pouch 178, thereby gaining access to first-aid pouch 174.

While various embodiments have been described above, it should be understood that they have been presented by way of example only, and not of limitation. Likewise, the various diagrams may depict an example architectural or other configurations and is intended to aid in understanding the features and functionality that can be included. The discovery is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present inventions. Also, a multitude of different constituent module names other than those depicted herein can be applied to the various partitions.

Although, described in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments, whether or not such embodiments are described and whether or not such features are presented as being a part of a described embodiment. Thus the breadth and scope of the present disclosure should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent.

As will become apparent to one of ordinary skill in the art after reading this document, the illustrated embodiments and their various alternatives can be implemented without confinement to the illustrated examples.

What is claimed is:

1. A system, comprising:
 a protective vest including a pocket to be worn by a user;
 a ballistic plate shaped to fit within the pocket; and
 a pouch including first-aid equipment, wherein the pouch comprises malleable material capable of being sealed, and a low profile form dimensioned to fit between the user and the ballistic plate upon the plurality of first-aid items being sealed in the pouch and upon positioning of the ballistic plate within the pocket.

2. The system of claim 1, wherein the protective vest contains an internal surface and an external surface, the external surface comprising the pocket for positioning the ballistic plate.

3. The system of claim 1, wherein the protective vest comprises an internal surface and an external surface, the internal surface comprising the pocket for positioning the ballistic plate and the pouch including first-aid equipment.

4. The system of claim 1, wherein the pouch is a first pouch, and the ballistic plate is a first ballistic plate, and further comprising a second pouch including first-aid equipment and a second ballistic plate,
 wherein the second pouch including first-aid equipment is located between the user and the second ballistic plate.

5. The system of claim 1, wherein the vest comprises a ballistic protective layer of soft armor.

6. A system, comprising:
 a protective vest, including a plurality of pockets, to be worn by a user;
 a first ballistic plate; and
 a first pouch including first-aid equipment,
 wherein the protective vest comprises an internal surface and an external surface,
 wherein the first pouch is located on the internal surface of the protective vest and is retained in place by a connector, and a first pocket is located on the external surface and is shaped for positioning of the first ballistic plate,
 and wherein the first pouch on the internal surface is positioned behind the first pocket and between the first ballistic plate and the user.

7. The system of claim 6, further comprising a layer of soft armor, wherein the first pouch including first-aid equipment is located between the first ballistic plate and the layer of soft armor.

8. The system of claim 1, wherein the protective vest comprises an aramid fiber.

9. The system of claim 1, wherein the pouch comprises a malleable material capable of being sealed and a thickness of less than about 1 inch.

10. The system of claim 1, wherein the first pouch is shaped to fit entirely behind the first ballistic plate.

11. The system of claim 1, wherein the first pouch comprises a thickness between about 0.2 and 0.4 inches.

12. The system of claim 1, wherein the malleable material is a reflective material.

13. The system of claim 1, wherein the malleable material is at least one of plastic, polyethylene, polypropylene, latex or rubber.

14. The system of claim 1, wherein the pouch is releasably connected to the protective vest.

15. The system of claim 2, wherein the pouch is releasably connected to the internal surface of the protective vest.

16. The system of claim 1, wherein the pouch contains a tear away strip.

17. The system of claim 1, wherein the pouch contains a handle.

18. The system of claim 1, wherein the pouch contains a rip cord.

19. The system of claim 6, wherein the first pouch comprises a thickness of between about 0.2 and 0.4 inches.

20. A kit, comprising:
 a sealable pouch; and
 a plurality of first-aid items, wherein the sealable pouch comprises malleable material and a low profile form dimensioned to fit between a user and a ballistic plate upon the plurality of first-aid items being sealed in the pouch and upon positioning of the ballistic plate within a vest worn by the user.

21. The kit of claim 20, wherein the sealable pouch comprises a thickness of less than about 1 inch.

22. The kit of claim 20, wherein the sealable pouch comprises a thickness of between about 0.2 and 0.4 inches.

23. The kit of claim 20, wherein the plurality of first-aid items are arranged in a prioritized order.

24. The kit of claim 23, wherein the prioritized order is based on order of expected use.

25. The kit of claim 20, where the plurality of first-aid items are detachably secured to a base.

26. The kit of claim 20, wherein the malleable material is a reflective material.

27. The kit of claim 20, wherein the malleable material is at least one of plastic, polyethylene, polypropylene, latex or rubber.

28. The kit of claim 20, further comprising a handle and a tear away strip.

29. The kit of claim 20, wherein the sealable pouch contains a rip cord.

30. The kit of claim 25, wherein the base comprises the same material as the sealable pouch.

31. The kit of claim 25, wherein the base is malleable.

* * * * *